(12) United States Patent
Klimko et al.

(10) Patent No.: US 7,112,588 B2
(45) Date of Patent: *Sep. 26, 2006

(54) USE OF PROTEASOME INHIBITORS TO TREAT DRY EYE DISORDERS

(75) Inventors: Peter G. Klimko, Fort Worth, TX (US); Mark R. Hellberg, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 108 days.

This patent is subject to a terminal disclaimer.

(21) Appl. No.: 10/808,061

(22) Filed: Mar. 24, 2004

(65) Prior Publication Data

US 2004/0180859 A1 Sep. 16, 2004

Related U.S. Application Data

(63) Continuation-in-part of application No. 10/150,191, filed on May 17, 2002, now Pat. No. 6,740,674.

(60) Provisional application No. 60/292,722, filed on May 21, 2001.

(51) Int. Cl.
*A61K 31/495* (2006.01)

(52) U.S. Cl. .................... 514/252.1; 514/912

(58) Field of Classification Search ............. 514/252.1, 514/9.12; 424/78.04
See application file for complete search history.

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,804,539 A | 2/1989 | Guo et al. | 424/450 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,966,773 A | 10/1990 | Gressel et al. | 424/489 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,403,841 A | 4/1995 | Lang et al. | 514/226.8 |
| 5,578,586 A | 11/1996 | Glonek et al. | 514/76 |
| 5,620,921 A | 4/1997 | Sullivan | 514/178 |
| 5,677,335 A | 10/1997 | Robertson et al. | 514/521 |
| 5,696,166 A | 12/1997 | Yanni et al. | 514/573 |
| 5,800,807 A | 9/1998 | Hu et al. | 424/78.04 |
| 5,958,912 A | 9/1999 | Sullivan | 514/177 |
| 6,071,904 A | 6/2000 | Ali et al. | 514/222.8 |
| 6,083,903 A | 7/2000 | Adams et al. | 514/2 |
| 6,096,733 A | 8/2000 | Lubkin | 514/182 |
| 6,107,289 A | 8/2000 | Sullivan | 514/178 |
| 6,153,607 A | 11/2000 | Pflugfelder et al. | 514/178 |

FOREIGN PATENT DOCUMENTS

| | | |
|---|---|---|
| JP | 10036289 | 2/1998 |
| WO | WO 95/31211 | 11/1995 |
| WO | WO 96/32105 | 10/1996 |
| WO | WO 98/35691 | 8/1998 |
| WO | WO 99/15183 | 4/1999 |
| WO | WO 99/22729 | 5/1999 |
| WO | WO 00/03705 | 1/2000 |
| WO | WO 00/43000 | 7/2000 |
| WO | WO 00/61168 | 10/2000 |
| WO | WO 00/64863 | 11/2000 |

OTHER PUBLICATIONS

Adams, "Proteasome Inhibitors as Therapeutic Agents" Expert Opinion in Therapeutic Patients, vol. 13(1), pp. 45-57 (2003).
Brignole et al., "Flow cytometric analysis of inflammatory markers in conjjnctival epithelial cells of patients with dry eyes," Database Medicine 'Online! May 2000; Database accession No. NLM10798650 XP002215304 abstract & *Investivative Ophthalmology & Visual Science*. United States, May 2000, vol. 41(6) pp. 1356-1363.
Corey et al., Total Synthesis and Biological Activity of Lactacystin, Omuralide and Analogs, *Chem. Pharm. Bull.*, vol. 47, pp. 1-10 (1999).
Dou, et al., "Pharmacological proteasome inhibitors and their therapeutic potential," *Exp. Opin. Ther. Patents*, vol. 10(8); pp. 1263-1272 (2000).
Dou, et al., "Proteasome inhibitors as potential novel anticancer agents," *Drug Resistance Updates*, vol. 2, pp. 215-223 (1999).
Elliott et al., "Proteasome inhibition: A novel mechanism to combat asthma," *J. Of Allergy and Clinical Immunology*, vol. 104(2);pp. 294-300 Aug. 1999.
Groettrup et al., "Selective proteasome inhibitors: modulators of antigen presentation?," *DDT*, vol. 4(2), pp. 63-71 (1999).
Iqbal, et al., "Proteasone inhibitors," *High Throughput Screening for Novel Anti-Inflammatories*, edited by M. Kahn, pp. 19-34 (2000).
Kisselev, et al., "Proteasome inhibitors: from research tools to drug candidates," *Chemistry & Biology*, vol. 8, pp. 739-758 (2001).

(Continued)

*Primary Examiner*—Zohreh Fay
(74) *Attorney, Agent, or Firm*—Patrick M. Ryan

(57) ABSTRACT

Proteasome inhibitors are useful for treating dry eye disorders and other disorders requiring the wetting of the eye.

4 Claims, No Drawings

OTHER PUBLICATIONS

Lee, et al., "Proteasome Inhibitors: valuable new tools for cell biologists," *Cell Biology*, vol. 8, p. 397-403 (1998).

Lemp et al., "Evaluation and differential diagnosis of keratoconjunctivitis sicca," Database Medline 'Online! Dec. 2000; Database accession No. NLM11128698 XP002215303 abstract & *The Journal of Rheumatology, Supplement.* Canada Dec. 2000, pp. 11-14.

Lemp, "Report of the National Eye Institute/Industry Workshop on Clinical Trials in Dry Eyes," *CLAO Journal*, vol. 21(4), pp. 221-231 (1995).

McCulley et al., "Tear Film Structure and Dry Eye," *Contactologia* vol. 20, pp. 145-149 (1998).

Marsh et al., "Topical Nonpreserved Methylprednisolone Therapy for Keratoconjunctivitis Sicca in Sjogren Syndrome," *Ophthalmology*, vol. 106(4), pp. 811-816 (1999).

Myung, et al., "The Ubiquitin-Proteasome Pathway and Proteasome Inhibitors," *Medicinal Research Reviews*, vol. 21(4), pp. 245-273 (2001).

Shine et al., "Keratoconjunctivitis Sicca Associated with Meibomian Secretion Polar Lipid Abnormality," *Arch. Ophthalmol.* vol. 116, pp. 849-852 (1998).

Soucy et al., "A Novel and Efficient Synthesis of a Highly Active Analogue of *clasto*-Lactacystin β-Lactone," *J. Am. Chem. Soc*, vol. 121, pp. 9967-9976 (1999).

Tauber et al., "Lacrimal Gland, Tear Film and Dry Eye Syndromes," *J. Adv. Exp. Med. Biology*, vol. 438, pp. (1998).

Wang et al., "Suppressionof NK-kappaβ-dependent proinflammatory gene expression in human RPE cells by a proteasome inhibitor," *Investigative Ophthalmoogy & Visual Science*, vol. 40(2), pp. 477-486 (1999).

USE OF PROTEASOME INHIBITORS TO TREAT DRY EYE DISORDERS

This application is a continuation-in-part application of U.S. application Ser. No. 10/150,191, filed May 17, 2002 now U.S. Pat. No. 6,740,674, which claims priority to U.S. Provisional Application, Ser. No. 60/292,722, filed May 21, 2001.

The present invention is directed to the treatment of dry eye disorders. In particular, the present invention is directed to the use of proteasome inhibitors in the treatment of dry eye and other disorders requiring the wetting of the eye in mammals.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes, The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye, Contactologia*, volume 20(4), pages 145–49 (1998); and Shine and McCulley, *Keratoconjunctivitis sicca associated with meibomian secretion polar lipid abnormality, Archives of Ophthalmology*, volume 116(7), pages 849–52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

U.S. Pat. No. 3,991,759 (Urquhart) discloses the use of ocular inserts in the treatment of dry eye. Other semi-solid therapy has included the administration of carrageenans (U.S. Pat. No. 5,403,841, Lang) which gel upon contact with naturally occurring tear film.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

The 20S proteasome is a complex of several enzymes that functions to degrade certain cellular proteins. Besides its involvement in the removal of misfolded or otherwise abnormal proteins, the proteasome also constitutes an integral part of several signaling mechanisms. One of these pathways involves inflammatory responses mediated by the nuclear transcription factor NF-κB. In its quiescent state NF-κB exists as a heterodimer with the protein Iκ-Bα, which masks the nuclear localization signals and DNA binding domain of the former protein. Under inflammatory conditions Iκ-Bα is phosphorylated, causing a conformational change which results in its tagging with multiple copies of the ubiquitin protein. Ubiquinated Iκ-Bα is recognized and degraded by the proteasome, which liberates NF-κB. The free protein is translocated to the nucleus, where it binds to the appropriate DNA sequence and upregulates the production of several inflammatory mediators, such as COX-2, iNOS, IL-1, and TNF-α. Inhibiting the activity of the proteasome may therefore represent a potential strategy for reducing excessive inflammation.

Some recent literature reports suggest that patients suffering from dry eye syndrome disproportionately exhibit the hallmarks of excessive inflammation in relevant ocular tissues, such as the lacrimal and meibomian glands. The use of the following types of pharmaceutically active compounds to treat dry eye patients has been disclosed: steroids

[e.g. U.S. Pat. No. 5,958,912; Marsh, et al., *Topical non-preserved methylprednisolone therapy for keratoconjunctivitis sicca in Sjogren syndrome*, Ophthalmology, 106(4): 811–816 (1999); Pflugfelder, et al. U.S. Pat. No. 6,153,607], cytokine release inhibitors (Yanni, J. M.; et. al. WO 0003705 A1), cyclosporine A [Tauber, *J. Adv. Exp. Med. Biol.* 1998, 438 (Lacrimal Gland, Tear Film, and Dry Eye Syndromes 2), 969], and 15-HETE (Yanni et. al., U.S. Pat. No. 5,696,166). Additionally, while proteasome inhibitors, have been disclosed as antiinflammatory agents for the treatment of various non-ocular (e.g., septic shock, ischemia-reperfusion injury, cancer, and graft rejection; see U.S. Pat. No. 6,083,903, WO 0043000, WO 0064863, WO 9922729, WO 9915183, WO 9835691, and WO 9632105) and ocular diseases (glaucoma and damage due to ocular surgery; see Jpn. Kokai Tokkyo Koho JP 10036289 A2, Chemical Abstracts Accession Number 128:226254), the use of proteasome inhibitors for the treatment of dry eye syndrome has not been previously suggested or disclosed.

SUMMARY OF THE INVENTION

The present invention is directed to methods for the treatment of dry eye and other disorders requiring the wetting of the eye, including symptoms of dry eye associated with refractive surgery such as LASIK surgery. According to the methods of the present invention, proteasome inhibitors are administered to a patient suffering from dry eye or other disorders requiring wetting of the eye. The proteasome inhibitors are preferably administered topically to the eye.

DETAILED DESCRIPTION OF THE INVENTION

Many proteasome inhibitors are known. Proteasome inhibitors useful in the methods of the present invention are those of formulas (I)–(III).

Formula (I):

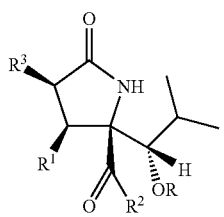

wherein:

R is H, alkyl, or acyl;

$R^1$ is $OR^4$, where $R^4$ is H or acyl, and $R^2$ is $SR^5$, where $R^5$ is alkyl, cycloalkyl, aryl, alkenyl, alkynyl, cycloalkenyl, heterocycloalkyl, or heterocycloalkenyl, all optionally containing one or more alkyl, halo, amino, acylamino, aminoacyl, hydroxyl, acyloxy, alkoxy, aryloxy, carboxyl, alkoxycarbonyl, or acyl groups; or $R^1$ is O and $R^2$ is bonded to $R^1$ to form a β-lactone ring; and $R^3$ is $CH_3$, $C_2H_5$, n- or $i-C_3H_7$, or n- or $i-C_4H_9$.

Formula (II):

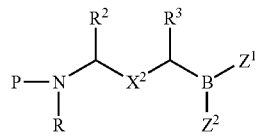

wherein:

P is morpholinylcarbonyl or 2- or 8-quinolinyl-, 2-quinoxalinyl-, 2- or 3-pyridyl-, piperazinyl-, 3-furanyl-, or 3-pyrrolylcarbonyl or -sulfonyl;

$X^2$ is CONH, $CH_2NH$, $CH(OH)CH_2$, $CH(OH)CH(OH)$, $CH(OH)CH_2NH$, CH:CH, $COCH_2$, $SO_2NH$, $SO_2CH_2$, or $CH(OH)CH_2CONH$;

R is H or alkyl;

$R^2$ and $R^3$ are the same or different and are H, alkyl, cycloalkyl, aryl, heterocyclyl, $CH_2R^5$, or alkyl-chalcogen;

$R^5$ is aryl, aralkyl, alkaryl, cycloalkyl, or heterocyclyl; and $Z^1$ and $Z^2$ are the same or different and are alkyl, hydroxy, alkoxy, or aryloxy.

Formula (III):

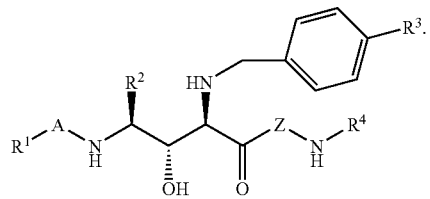

wherein:

A and Z represent a bond or an optionally substituted amino acid moiety;

$R^1$ is H, an amino protecting group (such as t-butoxycarbonyl or 9-fluorenylmethylcarbonyl), or a group $R^5Y$, where $R^5$ is H or a heterocyclylalkyl group and Y is CO, NHCO, NHCS, $SO_2$, OCO, or OCS;

$R^2$ represents the side chain of a natural amino acid or is alkyl, arylalkyl, heteroarylalkyl, cycloalkylalkyl, trimethylsilylmethyl, 2-thienylmethyl, or styrylmethyl;

$R^3$ is halo, alkyl, alkoxy, or hydroxyalkoxy; and $R^4$ is (2R)-hydroxyindan-(1S)-yl, (S)-2-hydroxy-1-phenylethyl, or 2-hydroxybenzyl, the phenyl rings of each being optionally substituted in the 4-position with a methoxy group.

The compounds of formulas (I)–(III) are known and can be made by known methods. For example, the synthesis of compounds included in formula (I) is disclosed in Adams, et. al., *J. Am. Chem. Soc.*, 121:9967 (1999). The synthesis of compounds included in formula (II) is disclosed in U.S. Pat. No. 6,083,903. The synthesis of compounds included in formula (III) is disclosed in WO 0064863.

Included within the scope of the present invention are the individual enantiomers of the compounds of the present invention, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 10 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 10 carbon atoms with at least one carbon-carbon double bond, the chain being optionally interrupted by one or more heteroatoms. The chain hydrogens may be substituted with other groups, such as halogen. Preferred straight or branched alkenyl groups include allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halo" or "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group, respectively, bonded from its oxygen atom to the carbon of a carbonyl group, the carbonyl group itself being bonded to another atom through its carbon atom.

Preferred for purposes of the present invention are those compounds of formula I wherein:

R is H, $CH_3CO$, $C_2H_5CO$, $Me_3CCO$, or PhCO;

$R^1$ is $OR^4$, where $R^4$ is H, $CH_3CO$, $C_2H_5CO$, $Me_3CCO$, or PhCO, and $R^2$ is $SR^5$, where $R^5$ is a defined above; or $R^1$ is O and $R^2$ is bonded to $R^1$ to form a β-lactone ring; and $R^3$ is $CH_3$, $C_2H_5$, n- or i-$C_3H_7$, or n- or i-$C_4H_9$.

Among the most preferred compounds of the present invention are the following compounds 1–4 (where Ac=an acetyl group):

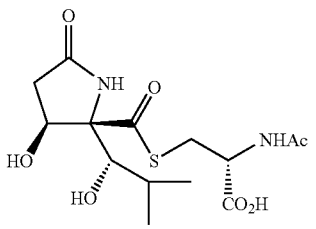

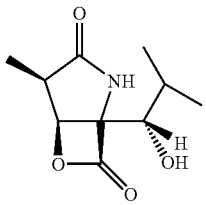

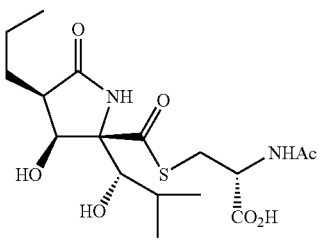

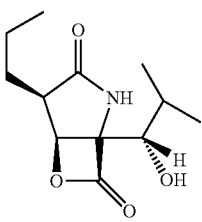

The syntheses of these compounds are disclosed in: Corey et. al., *Total Synthesis and Biological Activity of Lactacystin, Omuralide, and Analogs. Chem. Pharm. Bull.*, volume 47, pages 1–10 (1999); and Adams et. al., *A Novel and Efficient Synthesis of a Highly Active Analogue of clasto-Lactacystin β-Lactone. J. Am. Chem. Soc.*, volume 121, pages 9967–9976 (1999).

Also preferred for purposes of the present invention is the following compound of formula II:

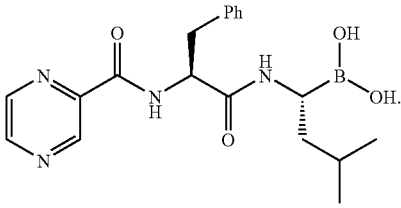

This compound of formula II is obtained when:
P is 2-quinoxalinylcarbonyl;
R is H;
$R^2$ is $CH_2R^5$;
$R^5$ is phenyl;
$X^2$ is CONH;
$R^3$ is 2-methylprop-1-yl; and
$Z^1$ and $Z^2$ are both OH.

According to the methods of the present invention, a composition comprising one or more proteasome inhibitors and a pharmaceutically acceptable carrier for topical ophthalmic administration or implantation into the conjunctival sac or anterior chamber of the eye is administered to a mammal in need thereof. The compositions are formulated in accordance with methods known in the art for the particular route of administration desired.

The compositions administered according to the present invention comprise a pharmaceutically effective amount of one or more proteasome inhibitors. As used herein, a "pharmaceutically effective amount" is one which is sufficient to reduce or eliminate signs or symptoms of dry eye or other disorders requiring the wetting of the eye. Generally, for compositions intended to be administered topically to the eye in the form of eye drops or eye ointments, the total amount of proteasome inhibitor will be about 0.0001 to 10 percent weight/volume ("% w/v"). For preferred topically administrable ophthalmic compositions, the total amount of proteasome inhibitor will be about 0.001–1% w/v.

The present invention is particularly directed to compositions useful in treating dry eye. Preferably, such compositions will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for proteasome inhibitors which are sparingly soluble in water.

The compositions of the present invention may also contain a surfactant. Various surfactants useful in topical ophthalmic formulations may be employed. The surfactant(s) may provide additional chemical stabilization of the compounds of formulas (I)–(III) and may further provide for the physical stability of the compounds. In other words, the surfactants may aid in preventing chemical degradation of the compounds of formulas (I)–(III) and also prevent the compounds from binding to the containers in which their compositions are packaged. As used herein, "an effective concentration of surfactant(s)" refers to a concentration that enhances the chemical and physical stability of the compounds of formulas (I)–(III). Examples of surfactants include, but are not limited to: Cremophor® EL, polyoxyl 20 ceto stearyl ether, polyoxyl 40 hydrogenated castor oil, polyoxyl 23 lauryl ether and poloxamer 407 may be used in the compositions. A preferred surfactant is polyoxyl 40 stearate. The concentration of surfactant will vary, depending on the concentration of the compound(s) of formulas (I)–(III) and optional ethanol present in the formulation. In general, however, the surfactant(s) concentration will be about 0.001 to 2.0% w/v. Preferred compositions of the present invention will contain about 0.1% w/v of polyoxyl 40 stearate.

The compositions of the present invention may also include various other ingredients, such as tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150–450 mOsm, preferably 250–350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6–7.5.

Antioxidants may be added to compositions of the present invention to protect the proteasome inhibitor compounds from oxidation during storage. Examples of such antioxidants include, but are not limited to, vitamin E and analogs thereof, ascorbic acid and derivatives, and butylated hydroxyanisole (BHA).

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more proteasome inhibitors. Examples or artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps").

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye or symptoms of dry eye. Preferably, such compositions will be administered topically. In general, the doses used for the above described purposes will vary, but will be in an effective amount to increase mucin production in the eye and thus eliminate or improve dry eye conditions. Generally, 1–2 drops of such compositions will be administered 1–10 times per day for the treatment of dry eye or other ocular disease or disorder. Preferably, 1–2 drops of the compositions will be administered 1–4 times per day.

A representative eye drop formulation is provided in Example 1 below.

EXAMPLE 1

| Ingredient | Amount (% w/v) |
| --- | --- |
| Compound of formula (I)–(III) | 0.0001–0.1 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.4 |
| Purified Water | q.s. 100% |

The above composition is prepared by the following method. The batch quantities of boric acid, sodium chloride, disodium edetate, and polyquaternium-1 are weighed and dissolved by stirring in 90% of the batch quantity of purified water. The pH is adjusted to 7.4±0.1 with NaOH and/or HCl. Under yellow light or reduced lighting, the batch quantity of the compound of formulas (I)–(III) as a stock solution is measured and added. Purified water is added to q.s. to 100%. The mixture is stirred for five minutes to homogenize and then filtered through a sterilizing filter membrane into a sterile recipient.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye which comprises administering to a mammal in need thereof a composition comprising a pharmaceutically acceptable carrier and a pharmaceutically effective amount of a proteasome inhibitor of the formula:

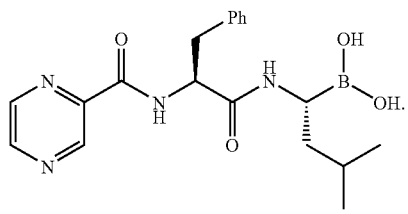

2. The method of claim 1, wherein the composition is topically administered to a mammal's eye.

3. The method of claim 1 wherein the pharmaceutically effective amount of the proteasome inhibitor is 0.0001–1% w/v.

4. The method of claim 1 wherein the dry eye is associated with refractive surgery.

* * * * *